United States Patent [19]

Fields

[11] 4,040,921

[45] Aug. 9, 1977

[54] PROCESS FOR BETA-HYDROXYALKYLSULFOXIDES

[75] Inventor: Ellis K. Fields, River Forest, Ill.

[73] Assignee: Standard Oil Company (Indiana), Chicago, Ill.

[21] Appl. No.: 709,781

[22] Filed: July 29, 1976

[51] Int. Cl.$^2$ .............................................. B01J 1/10
[52] U.S. Cl. ............................ 204/158 R; 204/162 R
[58] Field of Search ....................... 204/158 R, 162 R

[56] References Cited

U.S. PATENT DOCUMENTS 3,247,258  4/1966  Anderson ...................... 204/158 R

OTHER PUBLICATIONS

Schuller et al., I & EC Product Research & Development, vol. 3, No. 2, June 1964, pp. 97-100.

*Primary Examiner*—Howard S. Williams
*Attorney, Agent, or Firm*—William C. Clarke; Arthur G. Gilkes; William T. McClain

[57] ABSTRACT

Beta-hydroxyalkylsulfoxides are prepared by reacting an olefin and a thiol with oxygen in the presence of a dye sensitizer using visible light as an energy source at a temperature from $-10°$ to $70°$ C.

13 Claims, No Drawings

PROCESS FOR BETA-HYDROXYALKYLSULFOXIDES

BACKGROUND OF THE INVENTION

The field of this invention relates to a method for preparing β-hydroxyalkylsulfoxides by reacting an olefin, thiol and oxygen in the presence of a dye sensitizer using visible light as an energy source.

DESCRIPTION OF THE PRIOR ART

β-Hydroxyalkylsulfoxides have been found to be useful as detergents, insect repellants, anti-static agents and petroleum additives. Anderson, U.S. Pat. No. 3,247,258 which is incorporated by reference, discloses that in order to obtain β-hydroxyalkylsulfoxides in good yields, the mercaptan (or thiol), the olefin and the oxygen must be contacted about 80° C as substantially no reaction occurs below that temperature. Another critical feature according to Anderson is the method of carrying out the reaction. With certain olefins and mercaptans such as indene, styrene and thiophenol, the reaction occurs first by mixing the olefin and the mercaptan with the oxygen being bubbled thereafter through the mixture. Other patents such as Oswald et al, U.S. Pat. No. 3,043,824 and Goodhue et al, U.S. Pat. No. 3,210,243, which are each incorporated by reference, disclose preparing β-hydroxyalkylsulfoxides through (1) a co-oxidation route using a hydroperoxide or through (2) oxidation of the sulfide by means of hydrogen peroxide. Oswald indicates that the preparation of hydroperoxide products by olefin-mercaptan co-oxidation to the sulfoxide requires chain initiators, e.g., ultraviolet light or the addition of peroxide compounds (hydroperoxides). Such initiators, indicates Owsald, are especially important when aliphatic mercaptans or n-olefins are co-oxidized. In the absence of such catalysts, some co-oxidation reactions have extremely long induction periods and are not practical to carry out. Oswald indicates the olefin-mercaptan co-oxidation temperature may range from −50° C to 0° C, although Oswald does report two attempts to co-oxidize to the hydroperoxide at 20° C (Example 2) with a reaction time of 16 hours. Goodhue teaches that the preparation of the sulfoxide using hydrogen peroxide is a three-step synthesis through the sulfide which in turn is prepared from the mercaptan with epichlorohydrin.

The three methods have certain drawbacks such as requiring temperatures of at least 80° C, or a two step synthesis using the hydroperoxide route, or a three-step synthesis using hydrogen peroxide or a peracid. (Use a hydrogen peroxide on an industrial scale can be uneconomical because of cost.) Accordingly, there is a need for a simple economic process for producing β-hydroxyalkylsulfoxides in reasonable yield at ambient temperatures and short reaction times.

The general object of this invention accordingly is to produce β-hydroxyalkylsulfoxides directly from the mercaptan in good yield at ambient temperatures by co-oxidation with an olefin using oxygen to obtain an increased rate of reaction and short reaction time with consequent economic industrial advantage. Other objects appear hereinafter.

I have found that the objects of this invention can be obtained by a simple one-step process wherein a thiol or mercaptan and an olefin are co-oxidized with oxygen using visible light as an energy source in the presence of a dye sensitizer at ambient temperature and moderate pressures. Unlike the processes described by Anderson, Oswald and Goodhue, there is no need to use a temperature above 80° C nor to prepare the hydroperoxide first at a temperature of −50° C to 0° C followed by a conversion step to the hydroxysulfoxide, nor to prepare the sulfide first before preparing the sulfoxide. The process of this invention is characterized by its simplicity, ease of performance, good yields and relatively short reaction times.

While Kharasch et al. in J. Org. Chem. 16, 524 (1951) postulated that olefins, thiols and oxygen can react through the peroxide to give β-hydroxyalkylsulfoxides, Kharasch and other workers in the field (Anderson, Oswald, Goodhue among others) have not considered nor suggested that increased yields and reduced reaction times can be obtained by the direct one-step co-oxidation of mercaptans and olefins to the sulfoxide using oxygen and visible light with a dye sensitizer. The reaction mechanism postulated by Kharasch suggested the sulfide and hydroperoxide steps as separable reaction steps in achieving the hydroxyalkylsulfoxide.

SUMMARY OF THE INVENTION

This invention relates to an improved process for preparing beta-hydroxyalkylsulfoxides by reacting an olefin, thiol and oxygen in the presence of a dye sensitizer using visible light as an energy source at a temperature from about −10° to 70° C, preferably +10° to 40° C.

DETAILED DESCRIPTION OF THE INVENTION

Beta-hydroxyalkylsulfoxides are prepared by an improved process by reacting an olefin, a thiol and oxygen in the presence of a dye sensitizer using visible light as an energy source.

For the purpose of this invention, it is essential that a dye sensitizer be used. If visible light is employed without the use of the dye sensitizer, yields of beta-hydroxysulfoxides are substantially lower as is evidenced in the examples which follow. The low yield or even lack of reaction is consistent with Oswald, U.S. Pat. No. 3,043,824, in Examples III and IV wherein control solutions unexposed to ultraviolet light, but presumably to visible light, resulted in either little or no co-oxidation products.

In general, the process for preparing β-hydroxyalkylsulfoxides requires the reacting of an olefinically unsaturated compound containing 2 to 30 carbons atoms with a thiol in the presence of oxygen. These olefinically unsaturated compounds can be aliphatic, aromatic, cyclic and heterocyclic. These compounds are preferably terminal olefins and can be visualized as being of the formula RCH = CHR' where R' is preferably hydrogen. However, R and R' can be defined also as radicals and can be the same or different straight chain or branched chain alkyl groups containing 1 to 22 carbon atoms (such as methyl, ethyl, i-butyl, octyl, etc., to docosyl groups), preferably 4 to 18 carbon atoms; aralkyl groups as β-phenethyl, alkylated aryl groups as tolyl or xylyl, hetero-cyclic alkyl groups as picolyl and thiazylmethyl, cyclo alkyl groups as cyclopentylmethyl and cyclohexylmethyl, the last four containing 5 to 30 carbon atoms, preferably 6 to 24 carbon atoms, and the same groups containing substituents such as halogens (fluorine, chlorine, bromine and iodine), nitro, alkoxy (methoxy, ethoxy, propoxy, butoxy) or dialkyl-amino groups. R and R' can be joined and comprise a ring containing five to eight carbons atoms. Examples where R and R' are so joined to comprise a ring are cyclopentadiene and cyclooctatetraene. Examples of olefinically unsaturated aliphatic, aromatic and alicyclic compounds are ethylene, propylene, 1-butene, 1-pentene, 1-hexene, 1-octene, 1-decene, 1-dodecene, cyclohexene, cyclopentene, cyclooctene, cyclodocene, bicycloheptene, octahydronaphthalene, styrene, α-methylstyrene, 3-phenyl-1-propene, 1,1-diphenylethylene, 3,4-diphenylbutene-1, 1-and 2-vinylnaphthalene, 4-vinylbiphenyl, 1-vinyl anthracene, 2- and 4-vinylpyridine, 3-vinylthiophene, 2-vinylfuran, 2- and 4-vinylquinoline, 1-vinylphenanthridene, 2-vinyl-1,3,5-triazene.

Preferably the olefinically unsaturated compound comprises a hydrocarbon containing 4 to 16 carbon atoms such as butene-1 or tetra-decene-1 and hexadecene-1, and styrene. These are preferred because they are cheap and react readily, comprising easily available compounds for providing a range of derivative short-chain water-soluble compounds to long-chain oil-soluble compounds.

The thiol (or mercaptan) can be aliphatic, aromatic, alicyclic and heterocyclic and can be described as being of the general formula R"SH. R" can be a radical of from 1 to 24 carbon atoms, from methyl to tetracosyl radicals, preferably 1 to 16 carbon atoms. Examples of such thiols are methylthiol, ethylthiol, n- and isopropylthiol, n-, sec- and tert- butylthiol, n-hexylthiol, n-octylthiol, tert-octylthiol, n-dodecyl-thiol, n- and tert-hexadecylthiol, cyclohexylthiol, tetracosylthiol, thiophenol, thiocresol, 4-n-dodecylthiocresol, 4-tert-nonylthiocresol, pyridine-2-thiol, pyridine-4-thiol, thiophene-3-thiol, furan-2-thiol, quinoline-2-thiol, quinoline-4-thiol, phenanthridene-1-thiol, 1,3,5-triazene-2-thiol.

Preferably the thiol comprises a thiol containing 1 to 16 carbon atoms. These are preferred because they are cheap, reactive and extend the range of derivatives to cover these soluble in various inorganic and organic solvents. One or more hydrogens of the aliphatic, alicyclic and aromatic moieties such as methyl, ethyl, isobutyl, tolyl and phenyl moieties of the above described thiol compounds can be replaced with non-reactive radical groups such as halogens and nitro radicals and, on the alicyclic and aromatic moieties, by alkyl moieties.

The molar ratios of the reactants i.e., the thiols, olefins, oxygen, that can be used, can vary considerably. The thiol-olefin ratio is between 0.001 to 5 moles of thiol per mole of olefin. In the practice of my invention substantially equimolar amounts of olefin and thiol are preferred. Use of a solvent such as heptane, hexane, benzene, acetone, or dioxane at concentrations of 1 to 85 weight percent is convenient. When water-miscible solvents such as acetone or dioxane are used, water up to 50% by weight of organic solvent may be incorporated. In such cases, or when water is used with immiscible solvents such as heptane or benzene up to 50% by weight, phase-transfer agents such as cetyl trimethyl ammonium bromide, benzyl triethyl ammonium chloride, benzyl triphenyl phosphonium chloride, etc., are incorporated at concentrations of 0.001 to 1% by weight of total solvent.

Heptane is the preferred solvent: 10 to 40 weight percent is the preferred concentration range of the reactants.

In the practice of my invention it is essential that at least one optically sensitizing dye be used in conjunction with the application of visible light. For purposes of my invention, the term dye sensitizer can be defined as being an organic dye which increases spectral response. Typical dye sensitizers are fluorescein derivatives, methylene blue, certain porphyrins and polycyclic aromatic hydrocarbons. For purposes of this invention, suitable dye sensitizers include Rose Bengal, methylene blue and Eosin.

Rose Bengal and methylene blue are the preferred dye sensitizers dissolved in acetone at 0.1-5% by weight. Sufficient dye is added to give final concentrations of 0.02 to 1% by weight in the total reaction mixture; 0.05 to 0.25% by weight is preferred. Alternatively the dye may be introduced bound to an ion-exchange resin in a relatively insoluble form, e.g. anionic Rose Bengal or Eosin attached to the strongly basic anion exchange resin Amberlite IRA-400 (Rohm and Haas, Philadelphia) or cationic methylene blue attached to the strongly acidic cation exchange resin Amberlite IRC-200 (J. R. Williams et al., Tetrahedron Letters 4603 (1973)).

My reaction may be run in any type of open or sealed vessel, suitably agitated. A particularly useful apparatus for the reaction is the Parr Pressure Reaction Apparatus, Item No. 3911, made by the Parr Instrument Company of Moline, Illinois. This apparatus consists of a heavy-walled clear pyrex bottle connected with a tank of oxygen under pressure; the bottle is shaken vigorously during the reaction. Pressures of oxygen of 1to 250 psig may be used; 15 to 50 psig $O_2$ are convenient pressures in the laboratory although, commercially, pressures over 100 psig are preferred. The bottle is illuminated with visible light such as ordinary incandescent or photoflood bulbs of 50-500 watts, preferably mounted in reflectors with the light source 1-½ to 3 inches from the vessel.

The lamps used were General Electric 500 watt photoflood or incandescent bulbs and a General Electric 275 watt Sunlamp. Specifications of the G.E. 500 watt photoflood lamp require 1.61 radiated watts from 280 to 400 namometers, and 6.9 radiated watts from 400 to 700 namometers, the range of visible light. The G.E. Sunlamp has 4.47 radiated watts in the ultraviolet range from 280 to 400 namometers, and 7.03 radiated watts in the visible light range of 400 to 700 namometers.

Since the radiated wattage of the Sunlamp is greater than that of the incandescent bulb in the visible light range, it is indeed surprising that yield improvement and shortened reaction time occurred with use of visible light plus a dye sensitizer over that obtained by use of an ultraviolet light source as taught by the prior art, i.e., U.S. Pat. No. 3,043,824.

Reaction is continued until the calculated amount of oxygen has been absorbed as shown by pressure drop; times of 1 to 100 hours may be used, depending on the nature of the olefin, the thiol, and the pressure of oxygen. Workup generally consists of evaporating the reaction mixture at 30°-60° C. and 0.1-1 Torr, conveniently in a rotating RINCO evaporator (BUCHI Vacuum Rotary Evaporator ROTAVAPOR EL, Rinco Instrument Company, Inc., Greenville, Illinois).

In order to facilitate a clear understanding of the invention, the process of preparing β-hydroxyalkylsulfoxides from the reaction product of an olefin and a thiol with the use of oxygen, the following specific embodiments are described in detail. It should be understood, however, that the detailed expositions of the application of this process, while indicating preferred embodiments, are given by way of illustration only since various changes and modifications within the spirit and scope of the invention will become apparent to those skilled in the art from this detailed description.

EXAMPLE I

This example illustrates the increase in yield and increased reaction rate achieved by the method of the invention.

Solutions of 29.2 g. (0.2 mole) of tert.-octylthiol and 23 ml (0.2 mole) of freshly distilled styrene in 100 ml of n-heptane were shaken under 24 psig oxygen with and without visible and ultraviolet light and with and without dye sensitizer. The amount of oxygen absorbed was determined at 1, 2, 4, and 8 hours. Heptane and unreacted reagents were removed from the filtered solutions in vacuo at 40° C and 0.2 Torr in a Rinco evaporator to leave a residue, which constituted the product. The weights of product, $\beta$-phenyl-$\beta$hydroxyethyl tert.-octyl sulfoxide.

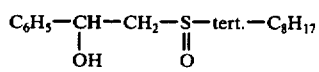

were determined. Results are shown in Table 1.

TABLE 1

| | Yields of $\beta$-Phenyl-$\beta$-Hydroxyethyl tert.-Octyl Sulfoxide | | | | |
|---|---|---|---|---|---|
| | | $O_2$ Absorbed, lbs. in Hrs. | | | Yield of Hydroxyalkylsulfoxides, grams |
| Run No | Conditions | 1 | 2 | 4 | 8 | (moles) |
| 1 | Dark | 0 | 0 | 0 | 0 | 0 |
| 2 | G.E. Sunlamp (No solvent) | 0 | 10 | 15 | 16 | 42.8 |
| | % of Total $O_2$ | — | 62 | 94 | 100 | (75.9) |
| 3 | G.E. Sunlamp + 10 ml acetone | 3 | 11.5 | 16 | 16.5 | 46.1 |
| | % of Total $O_2$ | 18 | 69 | 97 | 100 | (81.7) |
| 4 | Photoflood lamp (No solvent) | 0 | 1 | 3 | 6 | 9.6 |
| | % of Total $O_2$ | — | 16 | 50 | 100 | (17.0) |
| 5 | Photoflood lamp + 10 ml acetone | 0 | 2 | 9 | 14 | 38.7 |
| | % of Total $O_2$ | — | 14 | 64 | 100 | (68.6) |
| 6 | Photoflood lamp + 10 ml 1% methylene blue in acetone | 5.5 | 17 | 19 | — | 54.6 |
| | % of Total $O_2$ | 29 | 89 | 100 | | (96.8) |
| 7 | Photoflood lamp + 10 ml 1% Rose Bengal in acetone | 12.9 | 14.5 | 16.5 | 18.5 | 53.5 |
| | % of Total $O_2$ | 67 | 78 | 89 | 100 | (94.4) |

The data show the superior results achieved by use of visible light + dye and sensitizer + oxygen, Runs No. 6 and No. 7, in increased rate of reaction and yield of product. Runs No. 3 and No. 5 are controls with ultraviolet light (No. 3) and visible light (No. 5) together with the same amount of acetone as in Runs No. 6 and No. 7 (as acetone and ketones in general can act as sensitizers). Percent of total $O_2$ data indicate relative efficiency (yield versus time) of visible light plus dye sensitizer versus other conditions given.

Run No. 6 indicates that initial response of methylene blue is less than that of Rose Bengal as in Run No. 7 but overall response can be greater.

Run No. 7 shows a 15% increase in yield over Run No. 3 (94.4 divided by 81.7 × 100 − 100). Over 67% of the reaction occurred within the first hour of reaction of Run No. 7 while only 18% of Run No. 3 occurred in the first hour of reaction using ultraviolet light.

EXAMPLE II

Solutions of 21.34 ml (0.2 mole) of 1-pentene and 24.2 g (0.2 mole) of tert.-octylthiol in 100 ml of n-heptane were shaken under 24 psig oxygen under various conditions as in Example 1. The amount of oxygen absorbed was determined at 4, 8, and 24 hours. Work up was as in Example I. Heptane and unreacted reagents were removed from the filtered solutions in vacuo in a Rinco evaporator and the weights of product, $\beta$-hydroxypentyl tert.-octylsulfoxide

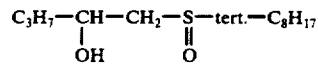

were determined. Results are shown in Table 2.

TABLE 2

| | Yields of $\beta$-Hydroxypentyl tert.-Octyl Sulfoxide | | | | |
|---|---|---|---|---|---|
| | | $O_2$ Absorbed, lbs. in Hrs. | | | Yield, |
| Run No. | Conditions | 4 | 8 | 24 | g (Mole %) |
| 1 | Dark | 0 | 0 | 0 | 0 |
| 2 | G.E. Sunlamp | 6 | 6 | 7 | 30.6 |
| | % of Total $O_2$ | 85 | 85 | 100 | (62.2) |
| 3 | G.E. Sunlamp + 10 ml acetone | 8 | 8 | 8.5 | 38.1 |
| | % of Total $O_2$ | 94 | 94 | 100 | (77.4) |
| 4 | Photoflood + 10 ml acetone | 2 | 7 | 8 | 34.4 |
| | % of Total $O_2$ | 25 | 87 | 100 | (69.9) |
| 5 | Photoflood + 10 ml 1% methylene blue in acetone | 10 | 13 | 14 | 44.7 |
| | % of Total $O_2$ | 71 | 92 | 100 | (90.9) |

The data show the superior results of Run No. 5 over the other runs in regard to increased rate of reaction and yield of product.

EXAMPLE III

The following example demonstrates the higher yield of purer product produced in a shorter time by use of oxygen with Rose Bengal as a dye sensitizer.

A mixture of 37.9 ml (0.2 mole) of 1-decene, 36 ml. (0.2 mole) of n-octyl mercaptan and 10 ml of 1% Rose Bengal in acetone was shaken under 23 psig $O_2$ and irradiation with a 500 watt photoflood lamp at 25° C. In 10 hours 15 lbs. $O_2$ were absorbed. The product weighed 44.4 g after being evaporated in a Rotovapor at 45° C and 0.2 Torr. It was recrystallized from n-heptane and filtered to give 26.4 g solid, mp 114° C, of β-hydroxydecyl n-octylsulfoxide,

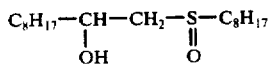

Analysis: Calcd. for $C_{18}H_{38}SO_2$: C, 67.9; H, 11.9; S, 10.1. Found: C, 67.5; H, 11.9; S, 9.9.

The same mixture without the Rose Bengal took 42 hours to absorb 13 lbs. $O_2$ and yielded 36.8 g of product of which 18.5 g was recrystallized as solid from n-heptane, mp 107°–109° C.

I claim:

1. A process for preparing β-hydroxyalkylsufoxides by reacting an olefinically unsaturated compound containing 2 to 30 carbon atoms and a thiol containing 1 to 24 carbon atoms with oxygen in the presence of a dye sensitizer using visible light as an energy source at a temperature within the range from about −10° to +70° C.

2. The process of claim 1 wherein the said olefinically unsaturated compound and said thiol are in molar ratios of from about 0.001 to 5.0 moles of thiol per mole of olefinically unsaturated compound.

3. The process of claim 2 wherein the molar ratio of said thiol and said olefinically unsaturated compound is substantially equal.

4. The process of claim 1 wherein said dye sensitizer is selected from the group consisting of methylene blue, Rose Bengal and Eosin.

5. The process of claim 1 wherein said olefinically unsaturated compound comprises a hydrocarbon containing from about 2 to 16 carbon atoms.

6. The process of claim 5 wherein said olefinically unsaturated compound comprises 1-pentene.

7. The process of claim 5 wherein said olefinically unsaturated compound comprises 1-octene.

8. The process of claim 5 wherein said olefinically unsaturated compound comprises 1-dodecene.

9. The process of claim 5 wherein said olefinically unsaturated compound comprises styrene.

10. The process of claim 1 wherein said thiol comprises a thiol containing from 1 to 16 carbon atoms.

11. The process of claim 10 wherein said thiol comprises t-octylthiol.

12. The process of claim 10 wherein said thiol comprises t-dodecylthiol.

13. The process of claim 10 wherein said thiol comprises n-octylthiol.

* * * * *